United States Patent
Chen et al.

(10) Patent No.: US 7,050,610 B2
(45) Date of Patent: May 23, 2006

(54) METHOD AND SYSTEM FOR IMPROVING THE SPATIAL RESOLUTION FOR STRAIN IMAGING

(75) Inventors: Jian-Feng Chen, Issaquah, WA (US); Patrick L. Von Behren, Bellevue, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 547 days.

(21) Appl. No.: 09/825,783

(22) Filed: Apr. 4, 2001

(65) Prior Publication Data

US 2002/0178833 A1 Dec. 5, 2002

(51) Int. Cl.
*G06K 9/00* (2006.01)

(52) U.S. Cl. ...................... 382/128; 600/410

(58) Field of Classification Search ................ 382/128, 382/166, 218, 282, 285, 294, 107; 324/309, 324/318; 424/9.51; 600/407, 410, 420, 600/437, 442, 443, 449, 450, 587; 128/898
See application file for complete search history.

(56) References Cited

U.S. PATENT DOCUMENTS

| | | | | |
|---|---|---|---|---|
| 5,178,147 A * | 1/1993 | Ophir et al. | ................. | 600/437 |
| 5,195,525 A * | 3/1993 | Pelc | ............................ | 600/410 |
| 5,678,565 A * | 10/1997 | Sarvazyan | ................... | 600/587 |
| 5,825,186 A * | 10/1998 | Ehman et al. | ............... | 324/309 |
| 5,833,634 A * | 11/1998 | Laird et al. | ................... | 600/587 |
| 5,860,931 A * | 1/1999 | Chandler | ..................... | 600/458 |
| 5,873,830 A * | 2/1999 | Hossack et al. | ............. | 600/447 |
| 5,876,342 A | 3/1999 | Chen et al. | .................. | 600/128 |
| 5,961,460 A * | 10/1999 | Guracar et al. | ............. | 600/440 |
| 6,494,834 B1 * | 12/2002 | Konofagou et al. | ......... | 600/438 |
| 6,508,768 B1 * | 1/2003 | Hall et al. | ................... | 600/443 |

OTHER PUBLICATIONS

Lorenz et al., "Diagnosis of Prostate Carcinoma using Multicompression Strain Imaging", IEEE 1998 Ultrasonic Symposium, pp. 1761-1764.*
"Elastography of Breast Lesions: Initial Clinical Results," Gara, et al., Dept. Of Radiology and Surgery, Georgetown University Medical Center, vol. 202, No. 1, Jan. 1997.

* cited by examiner

*Primary Examiner*—Yon J. Couso

(57) ABSTRACT

A method and system for quantification of strain imaging is disclosed. The method and system comprises performing a motion analysis on the at least two regions of interest. The method and system further includes providing a strain estimate for each of the at least two regions of interest and comparing the strain estimates of each of the at least two regions to quantify the strain for the at least two regions of interest. A system and method in accordance with the present invention provides for strain quantification based on conventional B-mode images. Using this technique, the strain of regions of interest (ROI) defined by users can be determined and quantitative comparisons can be effectively made in real time. The strain quantification can be used to determine tissue's properties and can potentially be applied in breast imaging as well as cardiac imaging.

14 Claims, 4 Drawing Sheets

METHOD AND SYSTEM FOR IMPROVING THE SPATIAL RESOLUTION FOR STRAIN IMAGING

FIELD OF THE INVENTION

The present invention relates generally to medical imaging and more specifically to a technique for quantifying ultrasound strain imaging.

BACKGROUND OF THE INVENTION

Strain imaging has been used in ultrasound medical imaging to differentiate between hard tissue and soft tissue. For example, since tumors are generally harder than normal tissues, strain imaging may be used evaluate solid breast masses. Strain images are created by comparing echo data obtained before and after a slight compression of the tissue. The results of the comparison are displayed as an image on which the hard areas appear dark and soft areas appear bright. Other black-and-white and other color scale may be employed for display. Typically strain imaging is accomplished by comparing the hard and soft tissue in a region of interest on a pixel by pixel basis using conventional ultrasound equipment.

Typically strain images are made from strain measure point by point, pixel by pixel, before and after compression. However, there are several problems with this type of method for quantifying the strain. First, there are artifacts that can be generated based on the probe usage over several points. Second, the system is time-consuming and tedious. Thirdly, other areas can distort the measured strain due to shadows, cavities and other areas of anomalies within the area being imaged.

Accordingly, what is desired is a system to more accurately and quickly quantify compression-induced strain the traditional brightness mode (B-mode) images. The present invention addresses such a need.

In recent years, several strain-imaging techniques have been proposed and developed by various research groups. In order to increase the spatial resolution for strain imaging, the adjacent local blocks, which are typically used to determine their displacements should be close enough. But there are technical difficulties for accurately determining the difference of displacements over these local blocks and generate the poor signal to noise ratio (SNR) for the strain images and therefore quantifying the strain measurements. Additionally, the levels of echo signals (which are related to the backscatter coefficients of insonifying tissue) from different types of tissues may be quite different, such as the echo signals from healthy breast tissue could be significantly different from the echo signals from breast cancer. These differences will cause additional errors for our motion estimation.

Accordingly, what is needed is a system and method for overcoming these problems. The present invention addresses such a need.

SUMMARY OF THE INVENTION

A method and system for quantification of strain imaging is disclosed. The method and system comprises performing a motion analysis on at least two regions of interest. The method and system further includes providing a strain estimate for each of the at least two regions of interest and comparing the strain estimates of each of the at least two regions to quantify the strain for the at least two regions of interest.

A system and method in accordance with the present invention provides for strain quantification based on conventional B-mode images. Using this technique, the strain of regions of interest (ROI) defined by users can be determined and quantitative comparisons can be effectively made in real time. The strain quantification can be used to determine tissue's properties and can potentially be applied in breast imaging as well as cardiac imaging.

DETAILED DESCRIPTION

The present invention relates to medical imaging and more specifically to a technique for quantifying tissue strain images. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Figure 1:
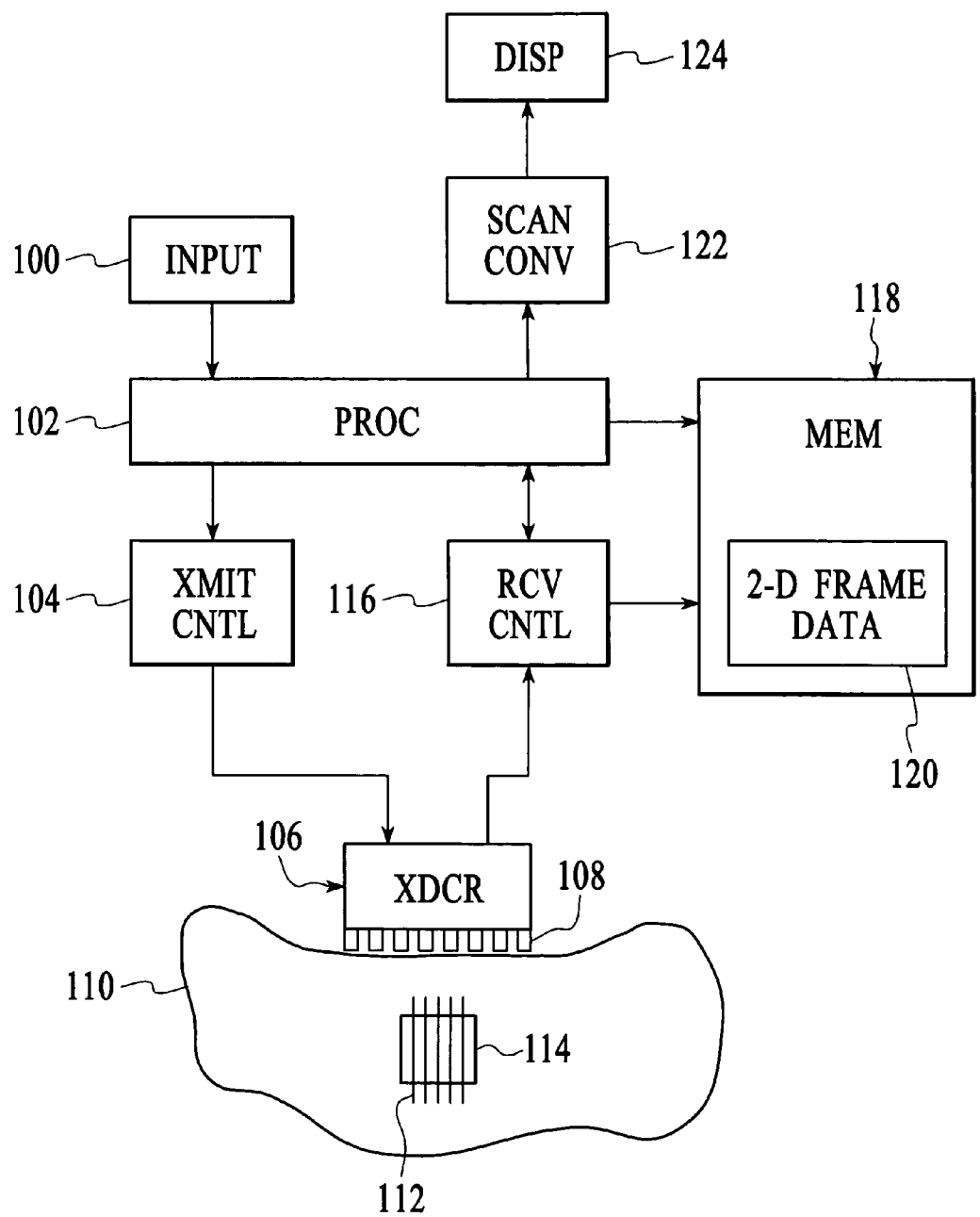
FIG. 1 is a simplified block diagram of an ultrasound system according to the present invention.

FIG. 1 is a simplified block diagram of an ultrasound system according to the present invention. The user enters the various conventional scan parameters into an input unit 100, which typically includes such devices as a keyboard, knobs and buttons. The input unit is connected to a processing system 102, which will typically be an electrically connected and cooperating group of processors such as microprocessors and digital signal processors; the processing system may, however, also be implemented by a single processor as long as it is fast enough to handle the various tasks described below.

As in known systems, the processing system 102 sets, adjusts, and monitors the operating parameters of a conventional transmission control circuit 104, which generates and applies electrical control and driving signals to an ultrasonic probe 106, which includes an array 108 of piezoelectric elements. As is well known in the art, the piezoelectric elements generate ultrasonic waves when electrical signals of the proper frequency are applied to them.

By placing the probe 106 against the body of a patient, these ultrasonic waves enter a portion 110 of the patient's body. By varying the phasing, amplitude, and timing of the driving signals, the ultrasonic waves are focused to form a series of scan lines 112 that typically fan out from the probe. Several such scan lines are shown extending into the patient's body in FIG. 3. A region of interest, that is, the region that the user wants to have an image of, is shown as an interrogation region or volume 114. The manner in which ultrasonic scanning signals are controlled, generated, and applied to a patient's body is well understood in the art and is therefore not described further. The interrogation volume 114 may be scanned using a series of substantially adjacent scan planes (each comprising several scan lines) that extend over a known depth.

Returning to FIG. 1, ultrasonic echoes from the waves transmitted into the body return to the array 108. As is well understood, the piezoelectric elements in the array thereby convert the small mechanical vibrations of the echoes into corresponding electrical signals. Amplification and other conventional signal conditioning is then applied to the return signals by a reception controller 116. This processing includes, as needed, such known signal conditioning as time-gating, gain compensation, and diffraction compensation in order to identify the echo signals that correspond to each scan plane of the interrogation volume 114.

The reception controller 116, all or part of which is normally integrated into the processing system 102, converts the ultrasonic, radio-frequency (RF) return signals (typically on the order of a few to tens of megahertz) into lower frequency ranges for processing, and may also include analog-to-digital conversion circuitry. This is well known in the art of ultrasonic imaging. The down-converted power values for the two-dimensional interrogation region are stored in a memory 118 as frame data 120, after conventional beamforming. Each set of frame data corresponds to one image frame, that is, to a cross section of the interrogation volume. Each frame of the image is represented and stored digitally as an array of acoustic power or intensity values for the image elements that make up the frame.

The interrogation region is normally not in the same shape as what the user wants to see displayed, and even when it is, the digital acoustic intensity values formed into beams are normally not in a form suitable for driving a conventional gray-tone or color display directly. The acoustic intensity values for an image frame are therefore applied to a conventional scan converter 122, which converts the digital acoustic values into display intensity or brightness values that are suitable for driving a display device 124. The display 124 is typically divided into a pattern of picture elements or "pixels" that make up an image that the user can view and interpret. Scan conversion and display are well-known features of an ultrasonic imaging system and are therefore not described further.

A system and method in accordance with the present invention provides for strain quantification based on conventional B-mode images. Using this technique, the strain of specific regions of interest (ROI) defined by users can be determined and quantitative comparisons can be effectively made in real time. The strain quantification can be used to determine tissue's properties and could be potentially applied in breast imaging as well as cardiac imaging.

To more particularly describe the features of the present invention, refer now to the following discussion in conjunction with the accompanying figures. In a preferred embodiment, a process is utilized to provide the strain quantifying arrangement. This process could be implemented in an algorithm which is part of a computer program. The program can be implemented in computer readable medium within the processor 102. The computer readable medium can be implemented in a disk drive floppy drive, CD-ROM, DVD or the like.

Figure 2:
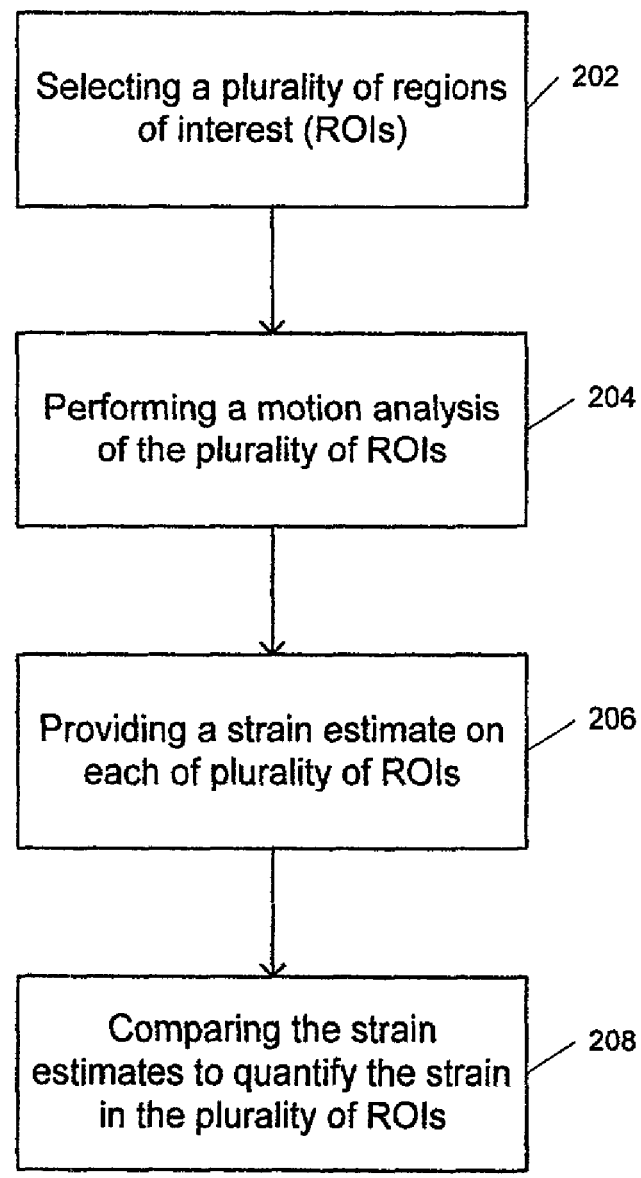
FIG. 2 is a flow chart of a system and method in accordance with the present invention.
Figure 3:
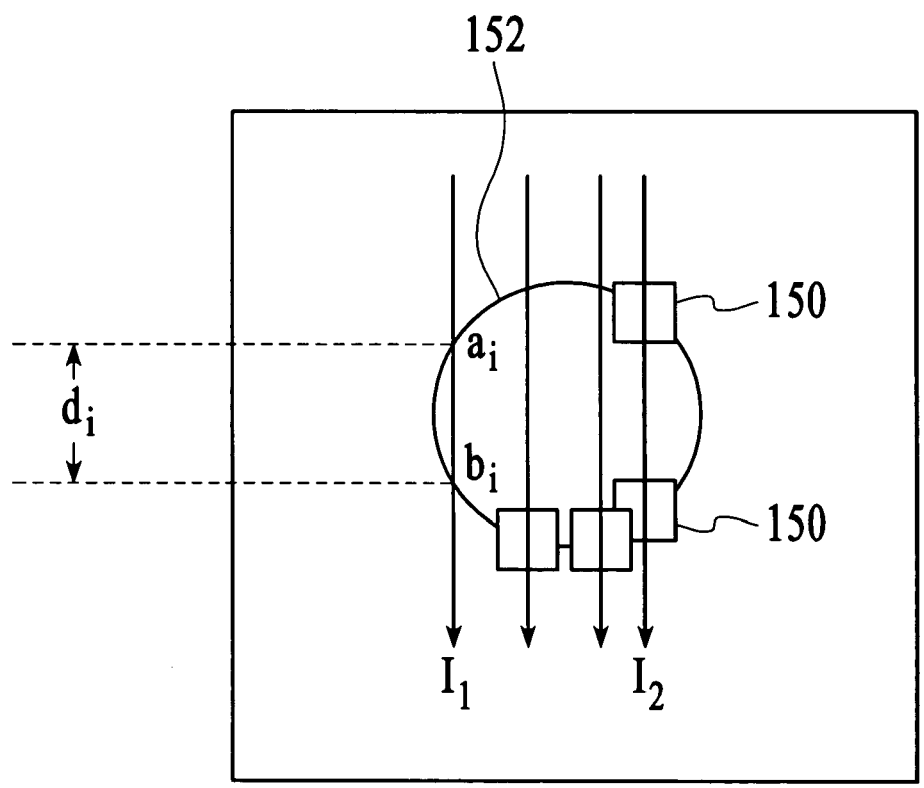
FIG. 3 shows a plurality of blocks generated for a region of interest.

FIG. 2 is a flow chart of a system and method in accordance with the present invention. First, at least two regions of interest (ROIs) are selected over one of a sequence of conventional B-mode images, via step 202. Several small local blocks, which touch the boundary of the ROI, are then generated over each of the regions of interest. FIG. 3 shows a plurality of blocks 150 generated for a region of interest 152. The size of the block 150 can not be too small, which could cause more statistical uncertainty. For an example, the size of block could be selected as 25×25 pixels.

The displacement or motion analysis of each block 150 is then determined, via step 204. In a preferred embodiment a conventional block matching technique is utilized. Accordingly, the block match technique would match a block in the first B-mode image (uncompressed) to a block in the second B-mode image (compressed) by computing the correlation of the block in the first image with each block of the same size in a defined search region of the second image. In an example, the size of a search region could be 32×32 pixels. In order to increase the computational speed and accuracy, the position of MSAD (the minimum of the Sum of Absolute Difference) of image data is searched instead of conventional correlation calculation. After determining all displacements for all local small blocks surrounding each region of interest, the strain value for each of the ROI can be quantitatively determined, via step 206 by the equation:

$$ST = \left\| \sum_{i=i_1}^{i_2} \frac{(a_i - b_i)}{d_i} \right\| \times 100\%$$

where $a_i$ and $b_i$ are the displacement components for two blocks, which cross over the boundary of a specific ROI, in the direction of i-th A-line. $d_i$ is a distance between the two blocks, and $i_1$ and $i_2$ are the index of A-line on B-mode image covering that specific ROI.

In clinical applications, two ways can be used to increase the accuracy of the strain value measurements. One way is to increase the compression from the probe, and another way is to increase the size of the regions of interest. For example, an ROI could be selected, which contains M×N pixels (M pixels in axial direction and N pixels in lateral direction). The correlation length over lateral direction (which is related to lateral B-mode image's spatial resolution) is described as n pixels. In that case, the minumum strain, which can be detected, is given by the equation:

$$ST_{\min} = \frac{100\sqrt{2}\,\delta}{M \times \sqrt{N/n}}\%$$

For an example, if the ROI is a square with 5.0×5.0 mm². The B-mode image is formed with a 7.5L40 probe with a depth of 4.0 cm. In that case, the minimum displacement estimation is about δ=0.25 pixel and the pixel size is about 0.1 mm, and lateral resolution (defined as the 6-db width of the point spread function) is about 0.5 mm. The minimum strain, which can then be detected, based upon the above-identified equation is $$ST_{\min} = \frac{100\sqrt{2} \times 0.25}{(5.0/0.1) \times \sqrt{(5.0/0.1)/(0.5/0.1)}}\% = 0.2\%$$

If the size of ROI is about 10.0×10.0 mm², the minimum strain, which can be detected, will be about 0.078%.

Accordingly, as above mentioned a strain estimate is performed for each ROI based upon the motion analysis, via step 206. Thereafter, the strain estimates are compared to quantify which region is hardest, via step 208.

Figure 4:
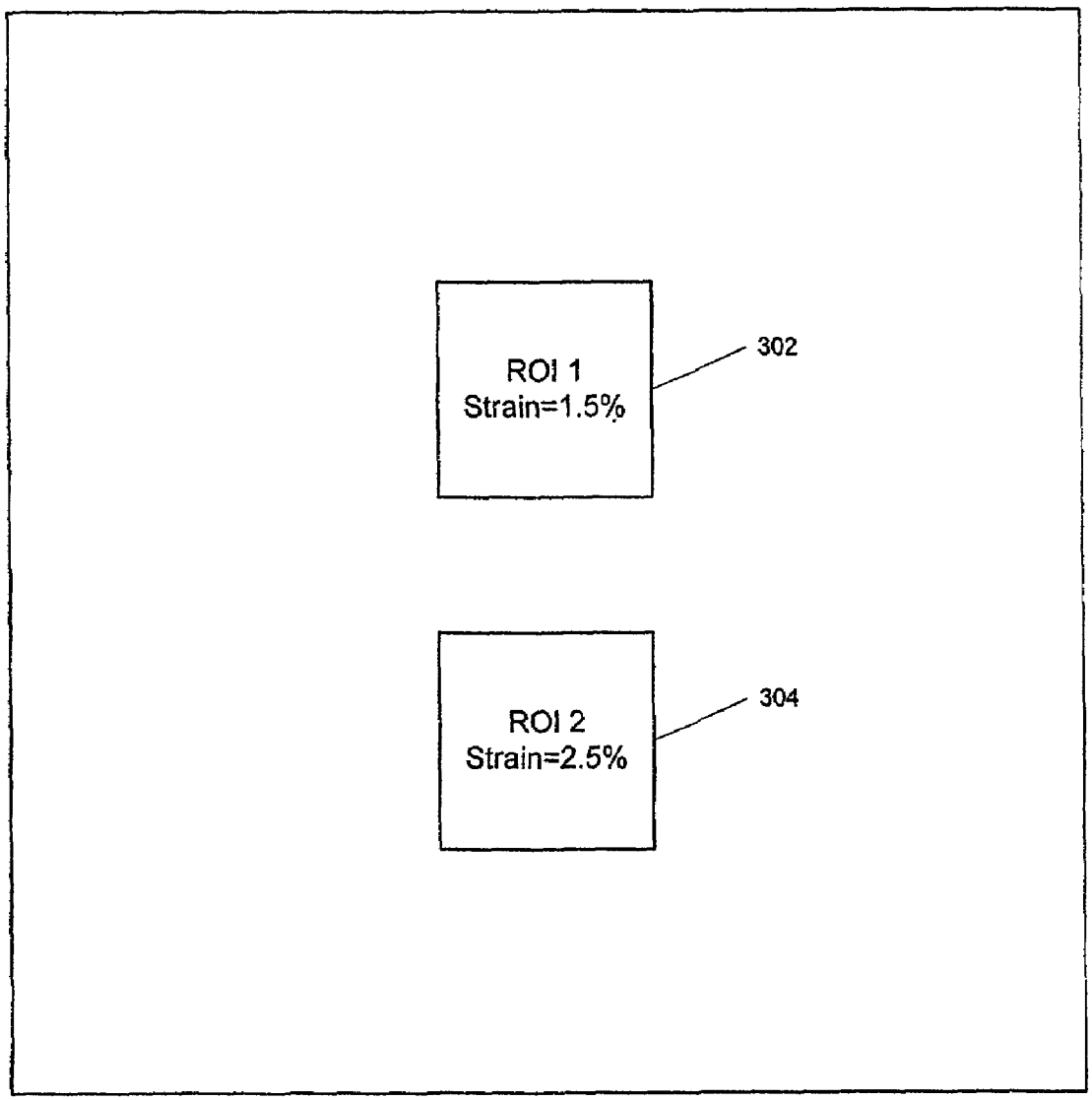
FIG. 4 illustrates two regions of interest in which the strain has been calculated.

The results from tests show that a method and system in accordance with the present invention could provide accurate quantitative information on tissue's strain, which could be important for quantifying tissue's properties. FIG. 4 illustrates two regions of interest, ROI 202 and ROI 204 in which the strain has been calculated in accordance with the present invention. As is seen, the strain estimate for the ROI 202 is 2.5% and the strain estimate for ROI 204 is 1.5%. Accordingly, as is seen ROI 204 has the harder tissue. In clinical applications it is desirable to select at least two ROIs to make an adequate comparison for strain quantification. The strain for two specific regions of interest (such as ROI 202 and ROI 204) can be determined by using the technique over B-mode images which is provided by a probe which provides an image depth of 4.0 cm. In this embodiment, the sizes of ROI are about 10.0×10 mm².

Although the present invention has been described in accordance with the embodiments shown, one of ordinary skill in the art will readily recognize that there could be variations to the embodiments and those variations would be within the spirit and scope of the present invention. Accordingly, although the analysis has been accomplished through a block match technique one of ordinary skill in the art readily recognizes that other types of motion analysis techniques could be utilized and they would be within the spirit and scope of the present invention. Accordingly, many modifications may be made by one of ordinary skill in the art without departing from the spirit and scope of the appended claims.

The invention claimed is:

1. A method for quantification of strain imaging comprising:
   (a) performing a motion analysis for tissue strain quantification on at least two selected regions of interest (ROI) before and after tissue compression;
   (b) providing a strain estimate for each of said at least two ROIs based upon said motion analysis;
   (c) comparing said strain estimates of each of said at least two ROIs to quantify strain for the at least two ROIs; and
   wherein said performing comprises:
      (a1) generating a plurality of blocks for each of said at least two ROIs; and
      (a2) utilizing a block matching technique to perform a motion analysis on each of said at least two ROIs.

2. The method of claim 1 wherein each of said plurality of blocks touch a boundary of said at least two ROIs.

3. The method of claim 1 wherein said providing is performed in accordance with equation:

$$ST = \left\| \sum_{i=i_1}^{i_2} \frac{(a_i - b_i)}{d_i} \right\| \times 100\%$$

where ST is strain estimate; and where $a_i$ and $b_i$ are displacement components for two blocks, which cross over a boundary of a specific ROI, in a direction of i-th A-line, $d_i$ is a distance between said two blocks, and $i_1$ and $i_2$ are indices along an A-line on a B-mode image covering said ROI.

4. A method for quantification of strain imaging comprising:
   (a) performing a motion analysis on a plurality of selected regions of interest (ROIs); said performing further comprising: (a1) generating a plurality of blacks for each of at least two ROIs; and (a2) utilizing a block matching technique to perform a motion analysis on each of said plurality of ROIs, wherein each of said plurality of blocks touch a boundary of said at least two ROIs;
   (b) providing a strain estimate for each of said plurality of ROIs based upon said motion analysis; and
   (c) comparing said strain estimates of each of said plurality of ROIs to quantify said strain for said at least two ROIs.

5. The method of claim 4 where said strain estimate is performed in accordance with equation:

$$ST = \left\| \sum_{i=i_1}^{i_2} \frac{(a_i - b_i)}{d_i} \right\| \times 100\%$$

where ST is strain estimate; and where $a_i$ and $b_i$ are displacement components for two blocks, which cross over a boundary of a specific ROI, in a direction of i-th A-line, $d_i$ is a distance between said two blocks, and $i_1$ and $i_2$ are indices along an A-line on a B-mode image covering that specific ROI.

6. A computer readable medium for quantification of strain imaging including program instructions for:
   (a) performing a motion analysis for tissue strain quantification on at least two selected regions of interest (ROI) before and after tissue compression;
   (b) providing a strain estimate for each of said at least two ROIs based upon said motion analysis;
   (c) comparing strain estimates of each of said at least two ROIs to quantify the strain for said at least two ROIs; and
   wherein said performing said motion analysis comprises:
      (a1) generating a plurality of blocks for each of said at least two ROIs; and
      (a2) utilizing a block matching technique to perform a motion analysis on each of said at least two ROIs.

7. The computer readable medium of claim 6 wherein each of said plurality of blocks touch a boundary of said at least two ROIs.

8. The computer readable medium of claim 6 wherein said providing said strain estimate (b) is performed in accordance with equation:

$$ST = \left\| \sum_{i=i_1}^{i_2} \frac{(a_i - b_i)}{d_i} \right\| \times 100\%$$

where ST is strain estimate; and where $a_i$ and $b_i$ are displacement components for two blocks, which cross over a boundary of a specific ROI, in a direction of i-th A-line, $d_i$ is a distance between said two blocks, and $i_1$ and $i_2$ are indices along an A-line on a B-mode image covering that specific ROI.

9. A computer readable medium for quantification of strain imaging having program instructions for:
   (a) performing a motion analysis on a plurality of selected regions of interest (ROIs); said performing further comprising: (a1) generating a plurality of blocks for each of said plurality of ROIs;
   (a2) utilizing a block matching technique to perform a motion analysis on each of said plurality of ROIs, wherein each of said plurality of blocks touch a boundary of said plurality of ROIs;

(b) providing a strain estimate for each of said plurality of ROIs based upon said motion analysis; and (c) comparing strain estimates of each of said plurality of ROIs to quantify said strain for at least two ROIs.

10. The computer readable medium of claim 9 wherein strain estimate is performed in accordance with equation:

$$ST = \left\|\sum_{i=i_1}^{i_2} \frac{(a_i - b_i)}{d_i}\right\| \times 100\%$$

where ST is strain estimate; and where $a_i$ and $b_i$ the displacement components for two blocks, which cross over a boundary of a specific ROI, in a direction of i-th A-line, $d_i$ is a distance between said two blocks, and $i_1$ and $i_2$ are indices along an A-line on a B-mode image covering that specific ROI.

11. A method for quantification of strain imaging comprising:

(a) performing a motion analysis on at least two selected regions of interest (ROI) before and after tissue compression;

(b) providing a strain estimate for each of said at least two ROIs said strain estimate being performed in accordance with equation:

$$ST = \left\|\sum_{i=i_1}^{i_2} \frac{(a_i - b_i)}{d_i}\right\| \times 100\%$$

wherein ST is strain estimate; and wherein $a_i$ and $b_i$ are displacement components for two blocks, which cross over a boundary of a specific ROI, in a direction of i-th A-Line, $d_i$ is a distance between said two blocks, and $i_1$ and $i_2$ are indices along an A-line on a B-mode image covering the ROI.

12. A method for quantification of strain imaging comprising:

(a) performing a motion analysis on a plurality of selected regions of interest (ROIs); said performing further comprising: (a1) generating a plurality of blocks for each of at least two ROIs; and (a2) utilizing a block matching technique to perform a motion analysis on each of said plurality of ROIs, wherein each of said plurality of blocks touch a boundary of said at least two ROIs;

(b) providing a strain estimate for each of said plurality of ROIs, said strain estimate performed in accordance with equation:

$$ST = \left\|\sum_{i=i_1}^{i_2} \frac{(a_i - b_i)}{d_i}\right\| \times 100\%$$

wherein ST is strain estimate; and wherein $a_i$ and $b_i$ are displacement components for two blocks, which cross over a boundary of a specific ROI, in a direction of i-th A-line, $d_i$ is a distance between two blocks, and $i_1$ and $i_2$ are indices along an A-line on a B-mode image covering that specific ROI; and (c) comparing strain estimates of each of said plurality of ROIs to quantify the strain for said at least two ROIs.

13. A computer readable medium for quantification of strain imaging including program instructions to perform a method comprising:

(a) performing a motion analysis on at least two selected regions of interest (ROI) before and after tissue compression;

(b) providing a strain estimate for each of said at least two ROIs, said strain estimate performed in accordance with equation:

$$ST = \left\|\sum_{i=i_1}^{i_2} \frac{(a_i - b_i)}{d_i}\right\| \times 100\%$$

wherein ST is strain estimate; and wherein $a_i$ and $b_i$ are displacement components for two blocks, which cross over a boundary of a specific ROI, in a direction of i-th A-line, $d_i$ is a distance between said two blocks, and $i_1$ and $i_2$ are indices along an A-line on a B-mode image covering that specific ROI; and (c) comparing strain estimates of each of said at least two ROIs to quantify the strain for at least two ROIs.

14. A computer readable medium for quantification of strain imaging having program instructions for:

(a) performing a motion analysis on a plurality of selected regions of interest (ROIs); said performing further comprising: (a1) generating a plurality of blocks for each of said plurality of ROIs;

(a2) utilizing a block matching technique to perform a motion analysis on each of said plurality of ROIs, wherein each of said plurality of blocks touch a boundary of said plurality of ROIs;

(b) providing a strain estimate for each of said plurality of ROIs, said strain estimate performed in accordance with equation:

$$ST = \left\|\sum_{i=i_1}^{i_2} \frac{(a_i - b_i)}{d_i}\right\| \times 100\%$$

wherein ST is strain estimate; and wherein $a_i$ and $b_i$ are displacement components for two blocks, which cross over a boundary of a specific ROI, in a direction of i-th A-line, $d_i$ is a distance between said two blocks, and $i_1$ and $i_2$ are indices along an A-line on a B-mode image covering that specific ROI; and (c) comparing strain estimates of each of said plurality of ROIs to quantify strain for at least two ROIs.

* * * * *